US012559466B2

(12) United States Patent
Shelke et al.

(10) Patent No.: US 12,559,466 B2
(45) Date of Patent: Feb. 24, 2026

(54) PROCESS FOR PREPARATION OF INTERMEDIATES

(71) Applicant: UPL LTD, Haldia (IN)

(72) Inventors: Santosh Ganpat Shelke, Mumbai (IN); Talati Paresh Vithaldas, Mumbai (IN); Jaidev Rajnikant Shroff, Dubai (AE); Vikram Rajnikant Shroff, Dubai (AE)

(73) Assignee: UPL LTD, Haldia (IN)

( * ) Notice: Subject to any disclaimer, the term of this patent is extended or adjusted under 35 U.S.C. 154(b) by 0 days.

(21) Appl. No.: 16/977,638

(22) PCT Filed: Jun. 4, 2018

(86) PCT No.: PCT/IB2018/053974
§ 371 (c)(1),
(2) Date: Sep. 2, 2020

(87) PCT Pub. No.: WO2019/171161
PCT Pub. Date: Sep. 12, 2019

(65) Prior Publication Data

US 2020/0399236 A1 Dec. 24, 2020

(30) Foreign Application Priority Data

Mar. 6, 2018 (IN) ............................. 201831008255

(51) Int. Cl.

| | |
|---|---|
| ***A01N 43/653*** | (2006.01) |
| ***A01N 25/12*** | (2006.01) |
| ***C07C 29/143*** | (2006.01) |
| ***C07D 249/12*** | (2006.01) |
| ***C07D 301/28*** | (2006.01) |

(52) U.S. Cl.
CPC ........... *C07D 301/28* (2013.01); *A01N 25/12* (2013.01); *A01N 43/653* (2013.01); *C07C 29/143* (2013.01); *C07D 249/12* (2013.01)

(58) Field of Classification Search
CPC ............................ A01N 43/653; C07D 249/12
See application file for complete search history.

(56) References Cited

U.S. PATENT DOCUMENTS 4,913,727 A * 4/1990 Stroech ................ A01N 43/653 504/191
5,099,040 A * 3/1992 Rosen ........................ C07F 3/02 260/665 G

FOREIGN PATENT DOCUMENTS

| | | | |
|---|---|---|---|
| CN | 106749057 | A | 5/2017 |
| CN | 107628928 | A | 1/2018 |
| DE | 3942240 | A1 | 6/1991 |
| DE | 4030039 | A1 | 3/1992 |

OTHER PUBLICATIONS

CN 107628928—machine English translation -original document publication date is Jan. 26, 2018.*
Wang (Synthesis of Prothioconazole, Nongyao, 48(3), 172-173, 201; 2009).*
Arnett (J. Am. Chem. Soc., 1965, 87 (7), pp. 1541-1553).*
Parin D Shah (International Journal of Advance Research in Science and Engineering IJARSE, vol. No. 3, Special Issue (01), Sep. 2014).*
Monticelli et al. (Monatsh Chem (2017) 148:37-48).*
International Search Report and Written Opinion for International Application PCT/IB2018/053974; International Filing Date: Jun. 4, 2018; Date of Mailing: Sep. 4, 2018; 11 pages.

* cited by examiner

*Primary Examiner* — Valerie Rodriguez-Garcia
(74) *Attorney, Agent, or Firm* — CANTOR COLBURN LLP

(57) ABSTRACT

Disclosed herein is a process for preparation of 1-chloro-2-(1-chlorocyclopropyl)-3-(2-chlorophenyl)propan-2-ol (compound of formula (I)) and 2-(1-chlorocyclopropyl)-2-[(2-chlorophenyl)methyl]oxirane (compound of formula (II)), which are synthetic intermediates in the preparation of triazole fungicides. The process comprises reacting a Grignard reagent of 2-chlorobenzyl halide with 1-chloro-1-chloroacetylcyclopropane, wherein said reaction is carried out at temperatures between 0° C. and 100° C. and characterized in that said reaction is carried out in a solvent system comprising methyl tetrahydrofuran and toluene.

3 Claims, No Drawings

PROCESS FOR PREPARATION OF INTERMEDIATES

TECHNICAL FIELD OF THE INVENTION

The present invention relates to the preparation of intermediates for triazole fungicides. Particularly, the present invention relates to the preparation of 1-chloro-2-(1-chlorocyclopropyl)-3-(2-chlorophenyl)propan-2-ol represented by compound of formula (I) and 2-(1-chlorocyclopropyl)-2-[(2-chlorophenyl)methyl]oxirane represented by compound of formula (II).

FIG. 1

(I)

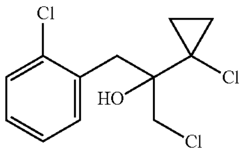

(II)

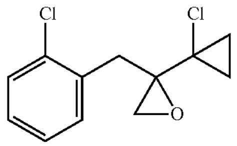

BACKGROUND OF THE INVENTION

The propane-2-ol derivative of the formula (I) and oxirane derivative of the formula (II) are valuable intermediates for preparation of triazole fungicides. One such example of triazole fungicide is prothioconazole. Prothioconazole is a sterol bio-synthesis inhibitor and systemic fungicide with protective, curative, eradicative and long-lasting activity.

U.S. Pat. No. 4,913,727 discloses the preparation of 1-chloro-2-(1-chlorocyclopropyl)-3-(2-chlorophenyl)propan-2-ol of compound of formula (I) and 2-(1-chlorocycopropyl)-2-[(2-chlorophenyl)methyl]oxirane of compound of formula (II) by reaction of 2-chlorobenzyl bromide with magnesium flakes in diethyl ether to get bromo-[(2-chlorophenyl)methyl]magnesium which further reacts with 1-chloro-1-chloroacetylcyclopropane in diethyl ether. However diethyl ether is not a suitable solvent for industrial manufacturing processes due to flammability hazards and processing difficulties.

U.S. Pat. No. 5,099,040 discloses a process for preparation of compound of formula (I) and compound of formula (II) by reaction of 2-chlorobenzylchloride with magnesium flakes in the presence of toluene and tetrahydrofuran to obtain chloro-[(2-chlorophenyl)methyl]magnesium which is further reacted with 1-chloro-1-chloroacetylcyclopropane in toluene and tetrahydrofuran to get compound of formula (I) and compound of formula (II). However the yield of the desired product is often not satisfying and the undesirable side product is formed in large quantities. Further, during the work up of reaction mass, THE is lost into the aqueous phase due its high water solubility. This causes the aqueous waste disposal problems and makes the process uneconomical.

Inventors of the present invention noted that a large amount of dimer 1-chloro-2-[2-(2-chlorophenyl)ethyl]benzene of compound of formula (III) (FIG. 2) is produced by following the above mentioned solvent system.

FIG. 2

(III)

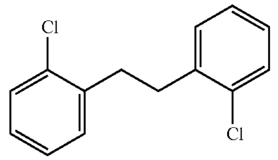

Consequently, the known methods for preparation of compound of formula (I) and compound of formula (II) may not be suitable for large scale production due to the causes such as insufficient yield, reaction conditions, and formation of large amount of undesirable side products. Considering the significance of compounds of formula (I) and compound of formula (II) for manufacturing fungicidally active compounds, there is a need for improved process for preparing such compounds.

OBJECTS OF THE INVENTION

It is an object of the present invention to provide an improved process for preparation of propan-2-ol derivative of the formula (I) and oxirane derivative of formula (II).

Another object of the present invention is to provide an improved process for preparing prothioconazole.

It is an object of the present invention to provide an economical process for preparation of compounds of formula (I) and compounds of formula (II) where water immiscible solvent is used which can be easily recovered.

SUMMARY OF THE INVENTION

The present invention provides a process for preparation of 1-chloro-2-(1-chlorocyclopropyl)-3-(2-chlorophenyl)propan-2-ol (compound of formula (I)) and 2-(1-chlorocyclopropyl)-2-[(2-chlorophenyl)methyl]oxirane (compound of formula (II)) or a mixture thereof, by reacting 2-chlorobenzyl halide with 1-chloro-1-chloroacetylcyclopropane wherein the reaction is carried out in a solvent system comprising methyl tetrahydrofuran.

The present invention further provides a process for preparation of compound of formula (I) and compound of formula (II) or a mixture thereof by reacting 2-chlorobenzyl chloride with 1-chloro-1-chloroacetylcycopropane wherein the reaction is carried out in a solvent system comprising methyl tetrahydrofuran.

The present invention provides a process for preparing prothioconazole comprising a) reacting 2-chlorobenzyl halide with 1-chloro-1-chloroacetylcyclopropane in a solvent system comprising methyl tetrahydrofuran; and
b) using the step (a) product to prepare prothioconazole.

The present invention further provides a process for preparing prothioconazole comprising c) reacting 2-chlorobenzyl halide with 1-chloro-1-chloroacetylcyclopropane in a solvent system comprising methyl tetrahydrofuran;
d) reacting the step (a) product with 1,2,4-triazole to produce 2-(1-chlorocyclopropyl)-1-(2-chlorophenyl)-3-(1H-1,2,4-triazol-1-yl)propan-2-ol; and
e) reacting the step (b) product with sulphur to produce prothioconazole.

The present invention further provides prothioconazole being substantially free of 1-chloro-2-[2-(2-chlorophenyl) ethyl]benzene of formula III:

(III)

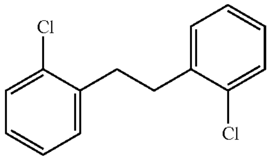

Further the invention provides use of solvent system according to the present invention for preparing compounds of the formula (I) and compounds of formula (II).

DETAILED DESCRIPTION OF THE INVENTION

It has now been found surprisingly that 1-chloro-2-[3-chloro-2-(1-chlorocyclopropyl)-2-methyl-propyl]benzene represented by compound of formula (I) and 2-(1-chlorocyclopropyl)-2-[(2-chlorophenyl)methyl]oxirane represented by compound of formula (II) or a mixture thereof can be prepared by Grignard reaction of 2-chlorobenzyl halide with 1-chloro-1-chloroacetylcyclopropane wherein the reaction is carried out in a solvent system comprising methyl tetrahydrofuran.

Inventors of the present invention unexpectedly observed that the inventive process drastically reduces the formation of compound of formula III as a byproduct. Such an advantage makes the inventive process suitable for upscale to industrial manufacturing of prothioconazole.

Inventors of the present invention also observed that the solvents of the present process can be recovered and recycled, thus making the process more industrially viable.

The inventors of the present invention further observed that certain compounds of formula (I) and compound of formula (II) or a mixture thereof are important intermediates for promising fungicidally active compounds.

The present invention thus provides a process for preparation of 1-chloro-2-(1-chlorocyclopropyl)-3-(2-chlorophenyl)propan-2-ol (compound of formula (I)) and 2-(1-chlorocyclopropyl)-2-[(2-chlorophenyl)methyl]oxirane (compound of formula (II)) or a mixture thereof by reacting 2-chlorobenzyl halide with 1-chloro-1-chloroacetylcyclopropane wherein the reaction is carried out in a solvent system comprising methyl tetrahydrofuran.

In an embodiment, the solvent system of the present invention comprises at least another solvent.

In an embodiment, the solvent system of the present invention comprises at least another solvent selected from solvents that are suitable for Grignard reagents.

In another embodiment, the solvent system of the present invention comprises at least another solvent selected from aliphatic or aromatic hydrocarbons.

In a preferred embodiment, the solvent system of the present invention comprises at least another solvent selected from aromatic hydrocarbons.

In yet another embodiment, the aliphatic solvents comprise hexanes and heptanes.

In another embodiment, the aromatic solvents comprise toluene and xylene.

In a preferred embodiment, the solvent system of the present invention comprises toluene.

Accordingly, one aspect of the present invention is to provide a process for preparation of compounds of formula (I) and compounds of formula (II) or a mixture thereof by Grignard reaction of 2-chlorobenzyl halide with 1-chloro-1-chloroacetylcyclopropane in a solvent system comprising methyl tetrahydrofuran.

In another embodiment, there is provided a process for preparation of compound of formula (I) and compound of formula (II) or a mixture thereof comprising Grignard reaction of 2-chlorobenzyl chloride and magnesium in a solvent system comprising methyl tetrahydrofuran to prepare magnesium complex followed by reaction with 1-chloro-1-chloroacetylcyclopropane.

The course of the process according to the invention can be illustrated in scheme 1 as below.

Scheme 1

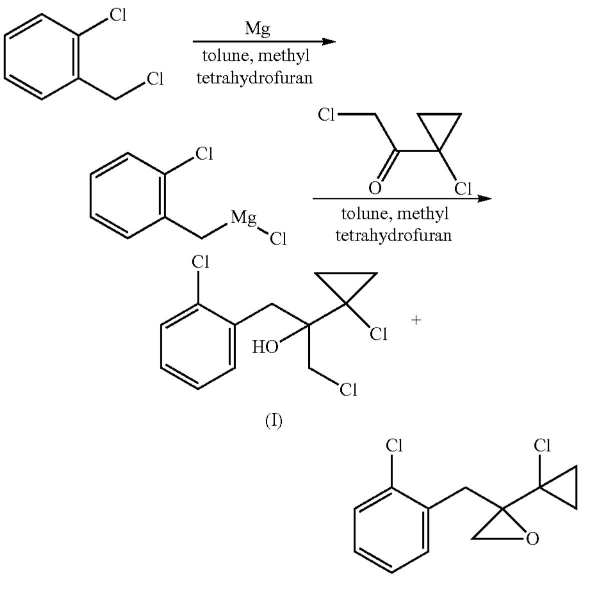

(I)

(II)

In an embodiment the solvent system of the present invention comprises methyl tetrahydrofuran and toluene.

In an embodiment the ratio of methyl tetrahydrofuran and toluene is in the range of 1:5 to 5:1.

In a preferred embodiment the ratio of methyl tetrahydrofuran and toluene is in the range of 1:3 to 3:1.

In an embodiment, the solvents used in the reaction are recovered and recycled.

In an embodiment the Grignard reaction is carried out by simultaneous addition of 2-chlorobenzyl chloride and magnesium.

In another embodiment the Grignard reaction is carried out by sequential addition of magnesium and 2-chlorobenzyl chloride.

In an embodiment the reaction is carried out at temperatures between 0° C. and 100° C.

In a preferred embodiment the reaction is carried out at temperatures between 0° C. and 40° C.

In an embodiment the inventive process produces compound of formula (III) in an amount less than 5%. In a preferred embodiment the inventive process produces compound of formula III in an amount less than 3%. In a preferred embodiment, the inventive process produces compound of formula III in an amount less than 1%.

In an embodiment the inventive process may further comprise catalysts or other solvents that are customary for Grignard reactions.

Another aspect of the present invention is to provide a process for preparing prothioconazole. This aspect too may have one or more embodiments described above.

Each of the embodiments described above may apply to this aspect as well. These embodiments are intended to be read as being preferred features of one or all the aspects described hereinabove.

Accordingly, in an embodiment, there is provided a process for preparing prothioconazole comprising:

a) Grignard reaction of 2-chlorobenzyl halide with 1-chloro-1-chloroacetylcyclopropane in a solvent system comprising methyl tetrahydrofuran;

b) Using the step a) product to produce prothioconazole.

In an embodiment, using the step a) product to produce prothioconazole comprises reacting the step a) product with 1,2,4-triazole to produce 2-(1-chlorocyclopropyl)-1-(2-chlorophenyl)-3-(1H-1,2,4-triazol-1-yl)propan-2-ol; and reacting this step's product with sulphur to produce prothioconazole.

Accordingly, in an embodiment, there is provided a process for preparing prothioconazole comprising:

c) Grignard reaction of 2-chlorobenzyl halide with 1-chloro-1-chloroacetylcyclopropane in a solvent system comprising methyl tetrahydrofuran;

d) Reaction of step a) product with 1,2,4-triazole to produce 2-(1-chlorocyclopropyl)-1-(2-chlorophenyl)-3-(1H-1,2,4-triazol-1-yl)propan-2-ol; and e) Reaction step b) product with sulphur to produce prothioconazole.

In an embodiment, the solvent system of the present invention comprises at least another solvent.

In an embodiment, the solvent system of the present invention comprises at least another solvent selected from solvents that are suitable for Grignard reagents.

In another embodiment, the solvent system of the present invention comprises at least another solvent selected from aliphatic or aromatic hydrocarbons.

In a preferred embodiment, the solvent system of the present invention comprises at least another solvent selected from aromatic hydrocarbons.

In yet another embodiment, the aliphatic solvents comprise hexanes and heptanes.

In another embodiment, the aromatic solvents comprise toluene and xylene.

In a preferred embodiment, the solvent system of the present invention comprises toluene.

It has been found that prothioconazole prepared using the process of the present invention is substantially free of the dimeric impurity of formula III.

In another embodiment, the present invention further provides prothioconazole being substantially free of 1-chloro-2-[2-(2-chlorophenyl)ethyl]benzene of formula III:

(III)

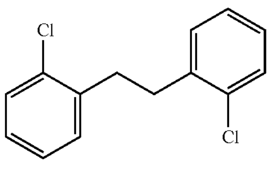

The term substantially free of is defined herein to mean that the prothioconazole contains less than 10%, preferably less than 5%, and most preferably less than 3% of the compound 1-chloro-2-[2-(2-chlorophenyl)ethyl]benzene of formula III.

In an embodiment the inventive process produces compound of formula (III) in an amount less than 5%.

In a preferred embodiment the inventive process produces compound of formula III in an amount less than 3%.

In another preferred embodiment, the process produces compound of formula III in an amount less than 1%.

The course of the process according to the invention in this embodiment can be illustrated in scheme 2 as below:

Scheme 2

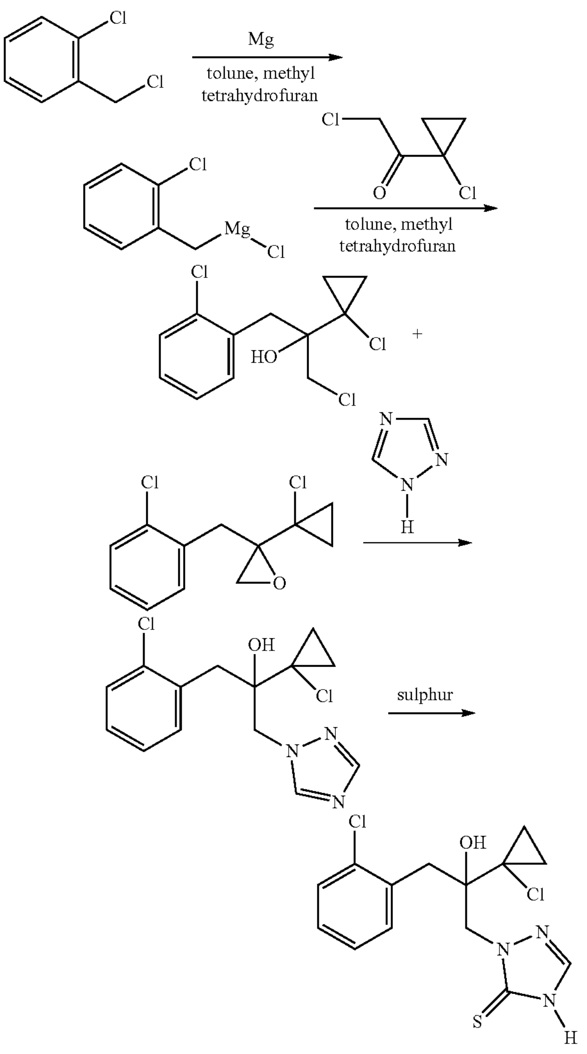

In a preferred embodiment there is provided a process for preparing prothioconazole comprising:

a) Grignard reaction of 2-chlorobenzyl chloride with 1-chloro-1-chloroacetylcyclopropane in a solvent system comprising methyl tetrahydrofuran;

b) Reacting step (a) product with 1,2,4-triazole and a base in an organic solvent to produce 2-(1-chlorocycopropyl)-1-(2-chlorophenyl)-3-(1H-1,2,4-triazol-1-yl)propan-2-ol: and c) Reacting step (b) product with sulphur powder in an organic solvent to produce prothioconazole.

In an embodiment the Grignard reaction of step (a) is conducted in a solvent system comprising toluene and methyl tetrahydrofuran wherein the ratio of methyl tetrahydrofuran and toluene is in the range of 1:5 to 5:1

In a preferred embodiment the ratio of methyl tetrahydrofuran and toluene for step (a) of the reaction is in the range of 1:3 to 3:1.

In an embodiment the Grignard reaction of step (a) is carried out by simultaneous addition of 2-chlorobenzyl chloride and magnesium.

In another embodiment the Grignard reaction of step (a) is carried by sequential addition of magnesium and 2-chlorobenzyl chloride.

The reaction with 1,2,4-triazole of step (b) is performed by known methods.

In the present invention the reaction of step (b) is achieved by reacting step (a) product with 1,2,4-triazole in an organic solvent in presence of a base.

In an embodiment, suitable bases for step (b) is selected from organic or inorganic base.

Preferably the base is selected from alkali or alkaline earth metal hydroxides, alkali metal carbonates or amines.

In another preferred embodiment the base for step (b) is selected from alkali metal carbonate such as potassium carbonate, sodium carbonate.

In an embodiment, suitable organic solvent for carrying out the step (b) of the process is selected from ethers, glycols, tetrahydrofuran, dioxane or polar solvents such as N-methyl pyrrolidone, dimethyl sulfoxide or dimethylformamide.

In a preferred embodiment the organic solvent for carrying out the step (b) of the process is selected from polar solvents such as N-methyl pyrrolidone, dimethyl sulfoxide or dimethylformamide.

The reaction with sulphur of step (c) is performed by known methods.

In the present invention the reaction with sulphur of step (c) is achieved by reacting step (b) product with sulphur powder in an organic solvent.

In an embodiment the suitable organic solvent for carrying out the step (c) of the process is selected from polar solvents such as N-methyl pyrrolidone, dimethyl sulfoxide or dimethylformamide.

According to another aspect, the invention provides use of solvent system according to the present invention for preparing compounds of the formula (I) and compounds of formula (II) or a mixture thereof.

The present invention further provides a method of using a solvent system comprising methyl tetrahydrofuran for preparing prothioconazole.

Therefore, in this embodiment, the present invention also provides prothioconazole prepared by a process which proceeds via the intermediates 1-chloro-2-(1-chlorocyclopropyl)-3-(2-chlorophenyl)propan-2-ol or 2-(1-chlorocyclopropyl)-2-[(2-chlorophenyl)methyl]oxirane or a mixture thereof, wherein said intermediates are prepared by reacting reacting 2-chlorobenzyl halide with 1-chloro-1-chloroacetylcyclopropane in a solvent system comprising methyl tetrahydrofuran.

In an embodiment the invention provides use of solvent system comprising methyl tetrahydrofuran for preparing compounds of the formula (I) and compounds of formula (II) or a mixture thereof.

In another embodiment the invention provides use of solvent system comprising toluene and methyl tetrahydrofuran for preparing compounds of the formula (I) and compounds of formula (II) or a mixture thereof.

In a preferred embodiment the present invention provides the use of solvent system comprising toluene and methyl tetrahydrofuran for preparing compounds of the formula (I) and compounds of formula (II) or a mixture thereof, wherein said process comprises Grignard reaction of 2-chlorobenzyl chloride and magnesium to prepare magnesium complex in said solvent system followed by reaction with 1-chloro-1-chloroacetylcyclopropane.

In another embodiment the present invention provides the use of solvent system comprising toluene and methyl tetrahydrofuran for preparing prothioconazole which is substantially free of compound of formula III.

The instant invention is more specifically explained by below examples. However, it should be understood that the scope of the present invention is not limited by the examples in any manner. It will be appreciated by any person skilled in this art that the present invention includes below examples and further can be modified and altered within the technical scope of the present invention.

EXAMPLES

The following examples described below are to illustrate the embodiments of the present invention and are not limiting the scope of the present invention.

Example 1: Preparation of 2-(2-chlorobenzyl)-2-(1-chlorocyclopropyl) Oxirane and 1-chloro-2-(1-chlorocyclopropyl)-3-(2-chlorophenyl)propan-2-ol (According to the Present Invention)

To a stirred mixture of magnesium flakes (29.0 g, 1.2 mol) and iodine (2.0 g, 0.0157 mol) in toluene (68 ml) and 2-methyl tetrahydrofuran (32 ml) was dropwise added a mixture of 2-chlorobenzylchloride (163.0 g, 1.0 mole) in toluene (230 ml) and 2-methyl tetrahydrofuran (110 ml) at 20-30° C. The reaction mixture was cooled to 0-10° C. and 1-chloro-1-chloroacetylcyclopropane (153 g, 0.95 mole) in 2-methyl tetrahydrofuran (40 ml) and toluene (120 m) was dropwise added to it and the reaction was stirred for 2 hours. Mixture of toluene and 2-methyl tetrahydrofuran was concentrated under reduced pressure and the reaction mass was cooled to 10° C. To the reaction mass was added water (350 ml) followed by hydrochloric acid (30%, 170 g) and was stirred for 3 hours at room temperature. The organic layer was separated, dried and concentrated under reduced pressure to obtain 247 g mixture of 2-(2-chlorobenzyl)-2-(1-chlorocyclopropyl) oxirane and 1-chloro-2-(1-chlorocyclopropyl)-3-(2-chlorophenyl)propan-2-ol. Crude mass 247 g is analyzed as 54.02% 2-(2-chlorobenzyl)-2-(1-chlorocyclopropyl) oxirane and 14.06% 1-chloro-2-(1-chlorocyclopropyl)-3-(2-chlorophenyl)propan-2-ol. Accordingly yield is 70.8% based on 1-chloro-1-chloroacetylcyclopropane. Dimer content: 3.5%.

Example 2: Preparation of 2-(2-chlorobenzyl)-2-(1-chlorocyclopropyl) Oxirane and 1-chloro-2-(1-chlorocyclopropyl)-3-(2-chlorophenyl)propan-2-ol (Comparative Example as per U.S. Pat. No. 5,099,040)

A mixture of magnesium flakes (17.0 g, 0.708 mol) and iodine (0.5 g) is treated with toluene (80 ml), tetrahydrofuran (20 m) and 2-chlorobenzychloride (1 g, 0.006 mole) at 20° C. A mixture of 2-chlorobenzychloride (97.0 g, 0.60 mole) in toluene (338 ml) and tetrahydrofuran (42 ml) is drop-wise added to it in the course of 5 hours at 50-55° C. After completion of addition the mixture is allowed to react for 30 minutes 50-55° C. The reaction mixture was cooled to 20° C. and unreacted magnesium is decanted. Into the decanted reaction mixture, 1-chloro-1-chloroacetylcyclopropane (89 g, 0.58 mole) in is dropwise added in the course of 45 minutes at 20-30° C. and the reaction was further stirred for 30 minutes. The reaction mixture is poured into the solution of concentrated sulfuric acid (24 g) and water (170 g) in the course of 30 minutes at 0-20° C. The organic layer was separated and washed with water. The organic layer was dried and concentrated under reduced pressure to obtain a mixture of 2-(2-chlorobenzyl)-2-(1-chlorocyclopropyl) oxirane and 1-chloro-2-(1-chlorocyclopropyl)-3-(2-chlorophenyl)propan-2-ol. Crude mass 145 g is analyzed as 27.69% 2-(2-chlorobenzyl)-2-(1-chlorocyclopropyl) oxirane and 10.36% 1-chloro-2-(1-chlorocyclopropyl)-3-(2-chlorophenyl)propan-2-ol. Accordingly yield is 49.92% based on 1-chloro-1-chloroacetylcyclopropane. Dimer content: 28.84%.

The following Table 1 describes Examples 3-11 prepared according to the present invention. Example 2 is a comparative sample prepared using THF and toluene as solvents.

TABLE 1

| Example No | 1-Chloro-2-(chloromethyl) benzene (g) | 1-chloro-1-cycloacetyl-cyclo propane (g) | 2-methyl tetrahydro-furan:Toluene (ml) | Oxirane derivative (%) | Propanol derivative (%) | Dimer (%) |
|---|---|---|---|---|---|---|
| 2 (comparative example) | 98 | 89 | 62:418* | 27.69 | 10.36 | 28.84 |
| 3 | 164 | 158 | 260:584 | 77.04 | 7.84 | 4.21 |
| 4 | 164 | 150 | 330:696 | 74.15 | 8.7 | 3.86 |
| 5 | 164 | 157 | 260:584 | 68.33 | 16.31 | 3.69 |
| 6 | 163 | 155 | 209:627 | 70.00 | 10.2 | 3.9 |
| 7 | 163 | 155 | 166:668 | 69.16 | 7.47 | 3.95 |
| 8 | 163 | 155 | 334:502 | 69.03 | 9.17 | 5.00 |
| 9 | 163 | 155 | 246:590 | 68.65 | 8.82 | 4.05 |
| 10 | 163 | 155 | 166:668 | 72.5 | 9.9 | 3.65 |
| 11 | 163 | 155 | 135:699 | 73.5 | 8.5 | 4.2 |

*Solvent used is tetrahydrofuran:Toluene

It is evident from the above table that the process according to the present invention led to the advantage of high yield of the product. Example 2 (comparative example) leads to a large amount of dimer as a side product thereby makes the process unsuitable.

Example 12: Preparation of Prothioconazole

Step a): Preparation of 2-(2-chlorobenzyl)-2-(1-chlorocyclopropyl) Oxirane and 1-chloro-2-(1-chlorocyclopropyl)-3-(2-chlorophenyl)propan-2-ol The process of example 1 is followed to prepare 2-(2-chlorobenzyl)-2-(1-chlorocyclopropyl) oxirane and 1-chloro-2-(1-chlorocyclopropyl)-3-(2-chlorophenyl)propan-2-ol mixture.

Step b): Preparation of 2-(1-chlorocyclopropyl)-1-(2-chlorophenyl)-3-(1,2,4-triazol-1-yl)propan-2-ol A mixture of 1,2,4-triazole (431 g), potassium carbonate (861 g) in dimethylformamide (DMF) (704 g) is heated to 80-85° C. for 1.0 hr. To this mixture is drop wise added 1-chloro-2-(1-chlorocyclopropyl)-3-(2-chlorophenyl)propa-2-ol and 2-(2-chlorobenzyl)-2-(1-chlorocyclopropyl) oxirane (577 g) in DMF (450 g) and the reaction mixture is heated to 80-85° C. for 3 hrs. The mixture is then cooled to room temperature and filtered to obtain residue. The residue thus obtained is washed with the portions of DMF, and then the filtrate is concentrated under reduced pressure to obtain a crude mass. The crude mass is then dissolved in toluene (900 g) and water (700 g) with continuous stirring at 65-70° C. for 1.0 hr. The resulting mixture is cooled and filtered off. The resulting filtrate is concentrated under reduced pressure and then crystallized in isopropanol to obtain 314 g of 2-(1-chlorocyclopropyl)-1-(2-chlorophenyl)-3-(1,2,4-triazol-1-yl)propan-2-ol.

Step C): Preparation of Prothioconazole

A mixture of DMF (80.0 g), 2-(1-chlorocyclopropyl)-1-(2-chlorophenyl)-3-(1,2,4-triazol-1-yl)propan-2-ol (80.0 g) and sulphur (21.0 g) are heated at 160-165° C. for 16 hrs. The reaction mixture is cooled to 20° C. and unreacted sulphur is filtered. The filtrate is concentrated under reduced pressure. To the residue is added toluene (350.0 g) and caustic solution (7.0%, 200 g) and stirred for 30 minutes at 70° C. Layers are separated. Toluene (350.0 g) is added to the aqueous layer and the solution is acidified with 15.0% HCl to pH 4-5. The mixture is cooled to 5° C. and the solid thus formed is washed with water followed by toluene (100.0 g). Crude solid is crystallized in methanol (100.0 g) after a charcoal treatment to obtain 70.0 g (98.0% purity) of prothioconazole.

The instant invention is more specifically explained by above examples. However, it should be understood that the scope of the present invention is not limited by the examples in any manner. It will be appreciated by any person skilled in this art that the present invention includes aforesaid examples and further can be modified and altered within the technical scope of the present invention.

The invention claimed is:

1. A process for preparation of a mixture of 1-chloro-2-(1-chlorocyclopropyl)-3-(2-chlorophenyl)propan-2-ol of formula (I)

(I)

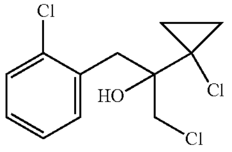

and 2-(1-chlorocyclopropyl)-2-[(2-chlorophenyl)methyl] oxirane of formula (II)

(II)

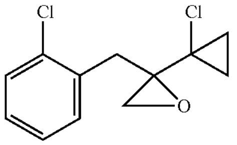

comprising reacting a Grignard reagent of 2-chlorobenzyl halide with 1-chloro-1-chloroacetylcyclopropane, wherein said reaction is carried out at temperatures between 0° C. and 40° C. and characterized in that said reaction is carried out in a solvent system comprising methyl tetrahydrofuran and toluene in a volume ratio of methyl tetrahydrofuran to toluene of 1:1.5 to 1:5, and further characterized that said mixture comprises 1-chloro-2-[2-(2-chlorophenyl)ethyl]benzene in an amount of 3 to 5% by weight.

2. A process for preparing prothioconazole comprising:

(a) reacting a Grignard reagent of 2-chlorobenzyl halide with 1-chloro-1-chloroacetylcyclopropane in a solvent system comprising methyl tetrahydrofuran and toluene in a volume ratio of methyl tetrahydrofuran to toluene of 1:1.5 to 1:5 to form a mixture of 1-chloro-2-(1-chlorocyclopropyl)-3-(2-chlorophenyl)propan-2-ol and 2-(1-chlorocyclopropyl)-2-[(2-chlorophenyl)methyl] oxirane, wherein said reaction is carried out at temperatures between 0° C. and 40° C., and said mixture comprises 1-chloro-2-[2-(2-chlorophenyl) ethyl]benzene in an amount of 3 to 5% by weight; and preparing prothioconazole from the product of step (a).

3. A process for preparing prothioconazole comprising:

(a) reacting a Grignard reagent of 2-chlorobenzyl halide with 1-chloro-1-chloroacetylcyclopropane in a solvent system comprising methyl tetrahydrofuran and toluene in a volume ratio of methyl tetrahydrofuran to toluene of 1:1.5 to 1:5 to form a mixture of 1-chloro-2-(1-chlorocyclopropyl)-3-(2-chlorophenyl)propan-2-ol and 2-(1-chlorocyclopropyl)-2-[(2-chlorophenyl)methyl] oxirane, wherein said reaction is carried out at temperatures between 0° C. and 40° C., and said mixture comprises 1-chloro-2-[2-(2-chlorophenyl) ethyl]benzene in an amount of 3 to 5% by weight;

(b) reacting the step (a) product with 1,2,4-triazole to produce 2-(1-chlorocyclopropyl)-1-(2-chlorophenyl)-3-(1H-1,2,4-triazol-1-yl) propan-2-ol; and (c) reacting step (b) product with sulfur to produce prothioconazole.

* * * * *